(12) United States Patent
Munoz Marquez et al.

(10) Patent No.: US 8,463,397 B2
(45) Date of Patent: Jun. 11, 2013

(54) HYPERTHERMIA DEVICES AND THEIR USES WITH NANOPARTICLES

(75) Inventors: Miguel Angel Munoz Marquez, Madrid (ES); Estefania Guerrero Garcia, Madrid (ES); Maria Asuncion Fernandez Camacho, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 457 days.

(21) Appl. No.: 12/670,493

(22) PCT Filed: Jul. 25, 2008

(86) PCT No.: PCT/IB2008/002780
§ 371 (c)(1),
(2), (4) Date: May 19, 2010

(87) PCT Pub. No.: WO2009/013630
PCT Pub. Date: Jan. 29, 2009

(65) Prior Publication Data
US 2011/0034974 A1 Feb. 10, 2011

(30) Foreign Application Priority Data
Jul. 26, 2007 (ES) .................................. 200702084

(51) Int. Cl.
*A61B 18/12* (2006.01)
(52) U.S. Cl.
USPC ............................ 607/101; 607/102; 607/113
(58) Field of Classification Search
USPC .................. 607/101–102, 113; 997/773, 904
See application file for complete search history.

(56) References Cited

U.S. PATENT DOCUMENTS

| | | | |
|---|---|---|---|
| 4,674,481 A * | 6/1987 | Boddie et al. | 600/10 |
| 5,097,844 A * | 3/1992 | Turner | 607/156 |
| 5,411,730 A | 5/1995 | Kirpotin et al. | |
| 5,507,743 A | 4/1996 | Edwards et al. | |
| 6,016,452 A * | 1/2000 | Kasevich | 607/101 |
| 6,097,985 A | 8/2000 | Kasevich et al. | |
| 6,167,313 A | 12/2000 | Gray et al. | |

(Continued)

FOREIGN PATENT DOCUMENTS

| ES | 2021075 | 4/1988 |
|---|---|---|
| GB | 2415374 A | 12/2005 |

(Continued)

OTHER PUBLICATIONS

N. Brusentsov et al., "Evaluation of ferromagnetic fluids and suspensions for the site-specific radiofrequency-induced hyperthermia of MX11 sarcoma cells in vitro", Journal of Magnetism and Magnetic Materials, 225: 113-117 (2001).

(Continued)

*Primary Examiner* — Linda Dvorak
*Assistant Examiner* — Jared W Pike
(74) *Attorney, Agent, or Firm* — Patrick J. Hagan; Dann, Dorfman, Herrell and Skillman, P.C.

(57) ABSTRACT

A hyperthermia device comprising a generator of radio-frequency electromagnetic fields, an amplifier of this signal, a transmitter of the electromagnetic field generated, and a direct temperature measurement system is disclosed for use with one or more nanoparticles capable of dissipating the energy of the applied electromagnetic field in the form of heat and it being possible to directly control the temperature of said nanoparticles.

22 Claims, 1 Drawing Sheet

U.S. PATENT DOCUMENTS

| | | | |
|---|---|---|---|
| 6,541,039 | B1 | 4/2003 | Lesniak et al. |
| 6,565,887 | B1 | 5/2003 | Gray et al. |
| 6,979,466 | B2 | 12/2005 | Lesniak et al. |
| 7,074,175 | B2 * | 7/2006 | Handy et al. .................. 600/9 |
| 7,174,217 | B2 * | 2/2007 | Rioux et al. .................. 607/99 |
| 7,627,381 | B2 * | 12/2009 | Kanzius et al. .............. 607/101 |
| 7,842,281 | B2 * | 11/2010 | Haik et al. .................... 424/9.3 |
| 7,945,335 | B2 * | 5/2011 | Xiang et al. .................. 607/101 |
| 2003/0180370 | A1 | 9/2003 | Lesniak et al. |
| 2005/0090732 | A1 | 4/2005 | Ivkov et al. |
| 2005/0249817 | A1 | 11/2005 | Haik et al. |
| 2006/0015159 | A1 | 1/2006 | Flores et al. |
| 2006/0171894 | A1 | 8/2006 | Takeyama |
| 2007/0151631 | A1 | 7/2007 | Fernandez Camacho et al. |
| 2007/0168001 | A1 | 7/2007 | Xiang et al. |
| 2011/0034916 | A1 * | 2/2011 | Te et al. ........................ 606/33 |

FOREIGN PATENT DOCUMENTS

| | | | |
|---|---|---|---|
| WO | 9743005 | | 11/1997 |
| WO | 0232404 | A2 | 4/2002 |
| WO | 03022360 | A2 | 3/2003 |
| WO | 2004089466 | A1 | 10/2004 |
| WO | 2004108165 | A2 | 12/2004 |
| WO | 2005116226 | A2 | 12/2005 |
| WO | 2006051542 | A1 | 5/2006 |
| WO | 2006116403 | A2 | 11/2006 |
| WO | 2007015179 | A1 | 2/2007 |
| WO | 2007027620 | A1 | 3/2007 |

OTHER PUBLICATIONS

K. Hamad-Schifferil et al., "Remote electronic control of DNA hybridization through inductive coupling to an attached metal nanocrystal antenna", Nature, 415: 152-155 (2002).

R. Herget et al., "Physical Limits of Hyperthermia Using Magnetite Fine Particles", IEEE Transactions on Magnetics, 34(5): 3745-3754 (1998).

A. Jordan et al., "Presentation of a new magnetic field therapy system for the treatment of human solid tumors with magnetic fluid hyperthermia", J. Magnetism and Magnetic Materials, 225: 118-126 (2001).

M. Kogan et al., "Nanoparticle-Mediated Local and Remote Manipulation of Protein Aggregation", Nanoletters, 6(1): 110-115 (2006).

A. Ponce et al., "Magnetic Resonance Imaging of Temperature-Sensitive Liposome Release: Drug Dose Painting and Antitumor Effects", J. Natl. Cancer Inst., 99: 53-63 (2007).

A. Templeton et al., "Water-Soluble, Isolable Gold Clusters Protected by Tiopronin and Coenzyme A Monolayers", Langmuir, 15: 66-76 (1999().

* cited by examiner

HYPERTHERMIA DEVICES AND THEIR USES WITH NANOPARTICLES

FIELD OF THE INVENTION

The present invention relates to hyperthermia devices, and more particularly to hyperthermia devices for use in the field of nanotechnology and the modification of nanostructured systems in applications where it is necessary to heat a specific area in a controlled way. The present invention further relates to the methods and uses of hyperthermia devices and nanoparticles in the field of biomedicine in applications such as the controlled release of drugs, the treatment of conditions such as tumors or amyloidosis.

BACKGROUND OF THE INVENTION

Thermal therapy consists of raising the temperature of living tissues until they are destroyed. This type of treatment can be divided into two main groups: hyperthermia in which the temperatures reach 46° C. and thermal ablation in which the temperature exceeds 47° C. Thermal therapy, and in particular hyperthermia, have been used to intensify radio- and chemotherapy treatments; tumorous tissues are more sensitive to heat than healthy tissues and additionally the temperature increase sensitises the cancer cells to chemotherapy and radiation treatments. In experimental and clinical oncology, hyperthermia treatments have already been used to raise the temperature of tumorous areas to 42-46° C.

Another possible application of hyperthermia in the field of biomedicine consists of controlling the aggregation of proteins which form deposits in the tissues called amyloids. If they accumulate in sufficient quantity, these deposits can alter the normal functioning of the tissue. Amyloidosis is involved in diseases such as diabetes mellitus, tuberculosis and rheumatoid arthritis, and there is also evidence linking amyloidosis with neurodegenerative diseases such as Alzheimer's and Parkinson's diseases.

Magnetic nanoparticles have been used in the diagnosis and monitoring of the growth of tumours. These particles, due to their magnetic properties, have served greatly to improve the contrast in nuclear magnetic resonance images. Another field in which nanoparticles have been used is in the controlled release of drugs, concentrating them in the affected area by the use of magnetic fields.

Currently, there are various microwave hyperthermia devices used for the treatment of tumorous tissues. These devices do not use nanoparticles and instead directly irradiate the diseased tissues with a microwave field which has destructive effects at a local level. This method is known by the name of interstitial hyperthermia.

Interstitial hyperthermia systems are rather aggressive towards the subject since, for maximum control of the irradiated area, antennas have to be implanted in the tissues by surgical methods, for example by means of a catheter (see U.S. Pat. No. 6,097,985), or by the insertion of an active radio-frequency electrode in the tumorous tissue which releases the energy of the electromagnetic field (see U.S. Pat. No. 5,507,743).

As an alternative to these aggressive techniques, several hyperthermia treatments have been proposed which are based on the use of magnetic fluids as a medium for dissipating the heat in living tissues. These fluids are made up of biocompatible magnetic fine particles or nanoparticles which are stabilized to prevent them from forming aggregates.

This type of procedure has the advantage that it does not involve the surgical implantation of antennas or electrodes in the diseased tissues, rather it uses magnetic fluids such as, for example, nanoparticles formed from magnetite (R. Hergt, W. Andrä, C. G. d'Ambly, I. Hilger, W. A. Kaiser, U. Richter, H-G. Schmidt, IEEE Trans. Mag. 34 (1998) 3745), a material having an acceptable biocompatibility, making it an ideal candidate for the preparation of magnetic fluids. In this case, the mechanisms for dissipation of the energy in the form of heat are mainly related to losses due to hysteresis and losses due to relaxation and friction, there being no losses due to induced Foucault currents. Each of these phenomena is discussed further below.

Losses due to hysteresis: Hysteresis is the tendency of a material to retain one of its properties, in this case magnetization (M), in the absence of the stimulus which has produced a change in that property, in this case an external magnetic field (H). In other words, if an external magnetic field is applied to a magnetic material, its magnetization will grow if the field increases to a maximum value ($H_{max}$). If the field is then decreased, the magnetization will not decrease as quickly as it increased. By representing the values of the external magnetic field compared to the magnetization, it can be seen that the relation between M and H not only is non-linear, it is not single-valued either. If the field is reduced to a minimum value ($H_{min}=-H_{max}$) and then the direction of the field is changed to make it increase again to $H_{max}$, the curve M against H turns out to be a closed curve known as a hysteresis curve or cycle (represented in FIG. 1). In all systems with hysteresis, there is an irreversible conversion of energy (or work) into heat throughout a complete cycle. In this case, it involves a conversion of magnetic energy into heat; this heat is equal to the area enclosed by the hysteresis curve.

Losses due to induced Foucault currents: When an electric conductor is in a time variable magnetic field (B(t)), the magnetic flux (F(t)) which passes through the conductor will also be variable with time. This variation in time induces a current in the conductor, the direction of which opposes the variation of the magnetic flux. The induced current has its origin in a generated electric field which produces a movement of free charges in the metal conductor, ultimately generating currents which, as a result of the Joule effect, will dissipate energy in the form of heat.

Losses due to relaxation and friction: In magnetic materials, domains with different orientations of the magnetic moment (m) are formed. In the grain boundaries of these domains, it can be considered that there are two metastable states of m, and corresponding to each state is an energy level, the difference corresponding with the anisotropy energy of the system ($E_{anis}$). In the presence of an external magnetic field (H), there is a probability of transition from one state to the other, which will give rise to a loss of energy in the form of heat, this mechanism also being known as relaxation due to the Néel effect. In the case of ferrofluids with a viscosity index, relaxation may also occur due to rotational Brownian movements of the magnetic particles, a very important phenomenon when the direction of the magnetic moment is strongly coupled to the particle and the movements due to the relaxation of m produce friction of the nanoparticles with the surrounding medium and/or other nanoparticles.

The magnetic properties of nanoparticles substantially depend on their size and structure. Ferromagnetic fluids have been investigated in respect of radio-frequency-induced hyperthermia in cells in vitro (N. A. Brusentsov, V. V. Gogosov, T. N. Brusentsova, A. V. Sergeev, N. Y. Jurchenko, A. A. Kuznetsov, O. A. Kutnetsov, L. I. Shumakov, J. Magn. Magn. Mater. 225 (2001) 113) and in solid tumours in human beings (A. Jordan, R. Scholz, K. Maier-Hauff, M. Johannsen, P.

Wust, J. Nadobny, H. Schirra, H. Schmidt, S. Deger, S. Loening, W. Lanksch, R. Felix, J. Magn. Magn. Mater. 225 (2001) 118).

Unfortunately, control of the temperature in the area of a tumour has so far proved to be very complicated to achieve. There is the risk of that overheating occurs, leading to healthy tissues being damaged as well. In order to solve this problem, recent attempts have been made to develop a different type of magnetic nanoparticle with a Curie temperature (i.e., the temperature above which a ferromagnetic body loses its magnetism, behaving in the same way as a purely paramagnetic material) of between 40 and 46° C. for possible application in medical hyperthermia treatments (Y. Haik, C-J. Chen, US Publication No. 2005/0249817). However, the effects on living organisms of the radio-frequency field necessary for producing a significant change in temperature are still not fully known. In addition, the materials used in nanoparticles with a controlled Curie temperature are transition metals, such as for example: nickel, copper, chromium, gadolinium, cobalt, manganese and zinc which are highly toxic to living creatures.

On the other hand, there are indirect observations in respect of the heating of metal gold nanoparticles under the action of an alternating electromagnetic field (K. Hamad-Schifferli, J. J. Schwartz, A. T. Santos, S. Zhang, J. M. Jacobson, Nature 415 (2002) 152; M. J. Kogan, N. G. Bastus, R. Amigo, D. Grillo-Bosch, E. Araya, A. Turiel, A. Labarta, E. Giralt, V. F. Puentes, Nanoletters 6 (2006) 110). The structural change of proteins or dehybridization of DNA chains bound to metal gold nanoparticles has been attributed to the dissipation of heat due to the Joule effect of the Foucault currents induced in the nanoparticles by the application of an electromagnetic field. The dissipation of heat, with the consequent rise in temperature of the medium, has always been determined in these systems from indirect observations related to the change in structure of the compounds with which the nanoparticles combine. Therefore, an exact and precise control of the temperature reached is not achieved, since it is only possible to estimate it indirectly.

In the field of the controlled release of drugs, hyperthermia has been proposed for use in drug dosing. There are studies relating to the release of drugs from liposomes (A. M. Ponce, B. L. Viglianti, D. Yu, P. S. Yarmolenko, C. R. Michelich, J. Woo, M. B. Bally, M. W. Dewhirst, J. Natl. Cancer Inst. 99 (2007) 53), which demonstrate that the dosing of the drugs is much more homogeneous and effective than by conventional methods. However, the application of the electromagnetic field as carried out until now in these systems involves the use of excessively aggressive techniques such as the surgical implantation of a microwave antenna for irradiating the affected area and inducing release of the drug.

Furthermore, in many cases, there are drugs which cannot pass through the biological barriers of living organisms, for example the cellular membrane or the haematoencephalic barrier; however such drugs could perform very important therapeutic functions within the cell or cerebrum. Nanoparticles bound to said drugs with a biocompatible coating are capable of passing through the aforementioned biological barriers; once through the barrier and with application of a radio-frequency field, the biocompatible coating changes its structure as a result of the rise in temperature, releasing the drug in the desired place.

Accordingly, there remains a problem in the art in employing hyperthermia in applications where it is necessary to heat a specific area in a controlled way.

SUMMARY OF THE INVENTION

Broadly, the present invention relates to a hyperthermia device that is capable of use in the field of biomedicine, typically in combination with the use of nanoparticles, the operation of which is compatible with biological systems and where the delivery of the hyperthermic effect is controllable.

Accordingly, in a first aspect, the present invention provides a hyperthermia device which comprises a generator of radio-frequency electromagnetic fields, an amplifier of this signal, a transmitter of the generated radio-frequency electromagnetic field, and a direct temperature measurement system, which is used together with one or more nanoparticles.

In addition, and specifically for when very high frequencies are used, the device of the invention also includes a Faraday cage for preventing damage to equipment or personnel as a result of the harmful effects of high doses of radiation.

The generator forming part of the device of the invention may be a network analyzer which, in addition to generating the signal, serves to determine impedances, coefficients of reflection, transmission and losses due to insertion, and thus allows investigations to be carried out as to the source of the heating up of one or more nanoparticles under the action of electromagnetic fields. By measuring the aforementioned coefficients and losses, it is possible to determine the attenuation of the signal and thus to calculate the energy dissipated by the nanoparticle or nanoparticles at a given frequency of the field.

The nanoparticle or nanoparticles which may be used in the device of the invention are all those which can heat up under the action of a radio-frequency electromagnetic field, such as, for example, noble-metal nanoparticles functionalized via metal-sulphur bonds with organic molecules or biomolecules, noble-metal nanoparticles functionalized via metal-ligand bonds, noble-metal nanoparticles protected by surfactant molecules with stabilization through bipolar interactions, magnetic nanoparticles functionalized directly or functionalized via a coating of noble metal. These nanoparticles heat up (hyperthermia) under the action of electromagnetic fields through losses due to hysteresis, Foucault currents or due to relaxation and friction. Examples of particularly preferred nanoparticles that may be employed with the hyperthermia devices of the present invention are disclosed in WO2002/032404, WO2004/108165, WO2005/116226 and WO2005/091704.

The radio-frequency electromagnetic field produced by the generator has a controlled intensity and frequency, the latter being between the values for very low frequency (VLF) signals and super-high frequency (SHF) signals.

The system for transmission of the radio-frequency electromagnetic field which forms part of the device of the invention is capable of focusing and concentrating the electromagnetic field in a specific region.

Geometric modification of the transmission devices will give rise to various forms of propagation of the electromagnetic field in space, which will allow studies to be carried out into new field transmission systems for directing the field and concentrating it in specific areas of space.

In addition, the device of the present invention is useful for any application in which localized heating is required, such as for example, and without this limiting the scope of the invention, in any application related to the modification of nanometric systems or related to biomedicine.

Accordingly, in a further aspect, the present invention relates to the use of the device of the present invention in biomedical applications overcomes the technical restrictions of hitherto existing hyperthermia apparatuses, since, for example in respect of the controlled release of drugs, the destruction of protein aggregates in amyloidosis or the localized destruction of tumours, it avoids having to use current hyperthermia systems involving invasive techniques, such as the implantation of antennas, for inducing release of the drug or destroying the tumour, thus avoiding one of the major disadvantages of currently existing hyperthermia systems.

In a further aspect, the present invention provides a hyperthermia device for use in a method of treatment of a condition which responds to hyperthermic heating of one or more nanoparticles, such as cancer or a condition mediated by amyloidosis.

In a further aspect, the present invention provides a method of heating one or more nanoparticles at a location, wherein the method employs a device which comprises (a) a generator of a radio-frequency electromagnetic field; (b) an amplifier of a radio-frequency electromagnetic field; (c) a transmitter of a radio-frequency electromagnetic field; and (d) a direct temperature measurement system, the method comprising the steps of:
  (i) introducing the nanoparticle at the location; and
  (ii) generating a radio-frequency electromagnetic field using the device which has a frequency and/or intensity capable of heating the nanoparticles.

Experimental studies in the literature show that the thermal energy of nanoparticles can be raised by irradiating them with electromagnetic fields. However, to date, control of the temperature has not been optimum. The direct measurement of the variations in temperature as incorporated in the device of the invention, with measurements preferably being carried out by infrareds or by methods based on the Seebeck effect, is an important new development in the field of hyperthermia, since, to date, evidence of heating of the nanoparticles has been obtained indirectly. In order to have any chance of observing a macroscopic change in the temperature of the medium in which the nanoparticles are placed, it is necessary to have a high power of electromagnetic field in the region where the nanoparticles are located. In order to utilize a high field power in a controlled way, it must be possible to control the energy of the field in an area of space as well as be able to modify and reproduce the conditions of the field in the same way as is achieved with the device of the present invention.

Embodiments of the present invention will now be described by way of example and not limitation with reference to the accompanying figures and examples.

DETAILED DESCRIPTION

Figure 2:
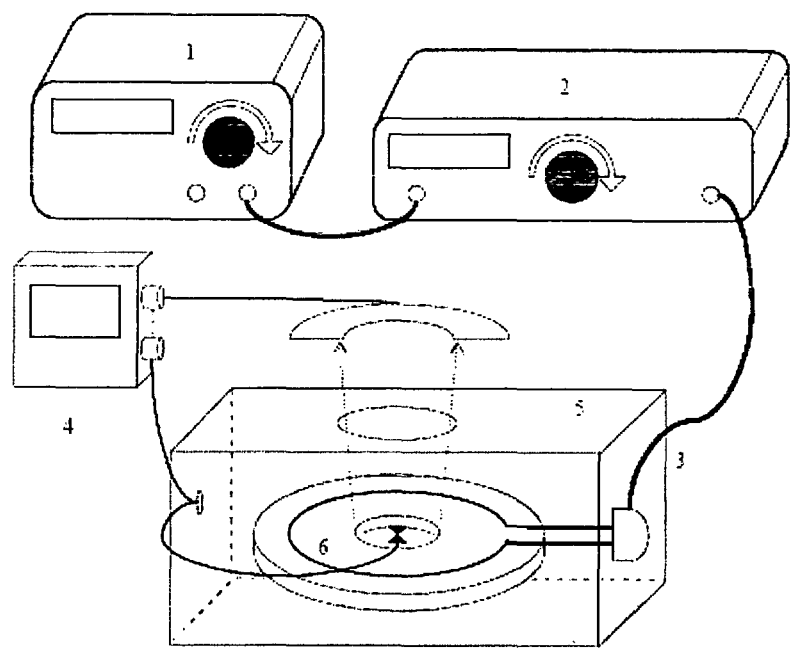
FIG. 2. Diagram of the device for generating, amplifying and transmitting radio-frequency fields for the heating of nanoparticles, said device comprising the following elements: (i) a generator of a radio-frequency electromagnetic field, (ii) an amplifier of the radio-frequency electromagnetic field, (iii) a transmitter of the radio-frequency electromagnetic field, (iv) a direct temperature measurement system, (v) a Faraday cage and (vi). One or more nanoparticles.

The device of the invention, which is used together with one or more nanoparticles (6), comprises the following elements as shown in FIG. 2.
1) A generator of a radio-frequency electromagnetic field which generates an electromagnetic pulse of controlled frequency and intensity which is transmitted to a radio-frequency amplifier. The frequency of this electromagnetic field is in the very low frequency (VLF) band up to the super-high frequency (SHE) band.
2) A broadband, low-noise radio-frequency electromagnetic field amplifier of radio-frequency signals, which works in the frequency range of the generator.
3) A transmitter of the radio-frequency electromagnetic field which, without this limiting the scope of the present invention, may consist of an antenna which, from the output signal of the amplifier, is capable of focusing and concentrating the generated radio-frequency electromagnetic field in a region of space.
4) A direct temperature measurement system.

When using frequencies which may interfere with electronic devices and/or affect personnel, the device of the invention may also include a Faraday cage (5) for radiation shielding purposes.

By way of example, the generator forming part of the device of the invention may be a network analyzer device which, in addition to generating the signal, serves to determine impedances, coefficients of reflection and transmission and insertion losses. Physical magnitudes which are related to the energy of the electromagnetic field which is dissipated and/or reflected throughout the experimental device, it thus being possible to investigate the origin and mechanisms of heating of nanoparticles subjected to the action of electromagnetic fields. For example, and without this limiting the scope of the present invention, by knowing the coefficients of reflection, transmission and losses due to insertion, together with the impedances of the experimental set-up, it is possible to determine the attenuation of the generated signal and consequently know with accuracy what signal is being transmitted to the nanoparticles. Taking that as a starting point, it is relatively straightforward to estimate the dissipated energy and, taking into account the frequency of the field, to relate it to the various heating mechanisms described above.

The device of the present invention generates controlled electromagnetic fields, in such a way that the nanoparticle or nanoparticles located in said electromagnetic field absorb part of the energy of the field and subsequently dissipate a large part of it in the form of heat, by means of any of the following mechanisms: losses due to hysteresis, losses due to induced Foucault currents, and losses due to relaxation and friction. The nanoparticles are collections of atoms or molecules which can reach sizes from 1 to 100 nm (where 1 nm is $10^{-9}$ m). On numerous occasions, only the criterion of size is used to define them. However, the characteristic which defines them as "nano", apart from their size, has to do with their physical properties. When the size of the building blocks of these systems becomes less than the characteristic length associated with any physical property, said property changes so that their behaviour can only be understood through the quantum theory.

The nanoparticle or nanoparticles which can be used with the device of the invention are all those nanoparticles, metallic or non-metallic, magnetic or non-magnetic, or a mixture of the aforementioned, which can be functionalized with organic molecules or biomolecules.

When one works with very small nanoparticles, there may be a certain lack of stability on reducing the coordination number of the atoms of which they are composed, as a result of which the nanoparticles will tend to form aggregates. In order to solve this problem, it is possible to stabilize the nanoparticles by using a protective molecule which binds to the surface atoms. This is what is known as functionalizing a nanoparticle. At the same time, if the functionalizing ligand or molecule is well chosen, it is possible for a functionalized nanoparticle to be capable of binding to a particular type of cell and/or molecule (very specific targets).

These nanoparticles can belong, without this limiting the scope of the present invention, to the following groups:

(a) Noble-metal nanoparticles (gold, palladium, copper, etc.) functionalized via metal-sulphur bonds with organic molecules or biomolecules. These nanoparticles have metallic and/or magnetic properties depending on the size and on the functionalization chain and can heat up through the various mechanisms of hysteresis, relaxation or induced currents.

(b) Noble-metal nanoparticles functionalized via metal-ligand bonds. The ligands may be phosphines or halides amongst others. They may be functionalized with biomolecules as a result of joining up with the ligand and they have metallic and/or magnetic properties depending on the size and type of ligand. These nanoparticles can be heated by the various mechanisms of hysteresis, relaxation or induced currents.

(c) Noble-metal nanoparticles protected by surfactant molecules with stabilization via dipolar interactions. They have metallic properties depending on size and can be heated by the mechanisms of induced currents.

(d) Magnetic nanoparticles (for example, iron-based) functionalized directly or functionalized via a coating of noble metal. They have magnetic properties depending on size and can be heated by the mechanisms of hysteresis and magnetic relaxation. The noble-metal coating component can behave in a similar way to the particle type (a) described in this section.

Figure 1:
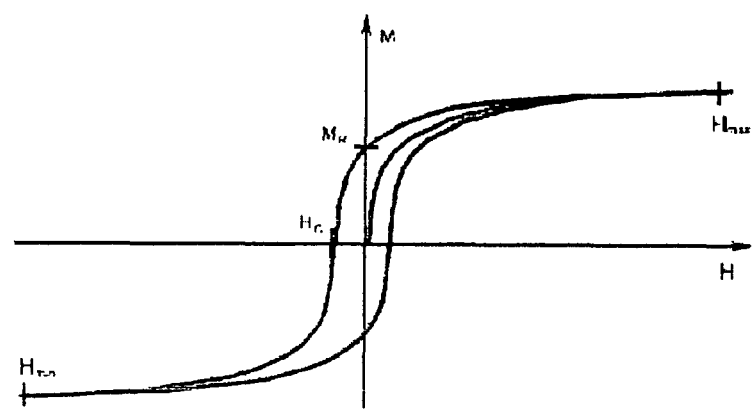
FIG. 1. Graphic representation of a hysteresis curve.

Both the metallic character in nanoparticles of type a), b) and c), and the magnetic character in nanoparticles of type d), and occasionally a) and b), are properties which depend, inter alia, on the size of the nanoparticles. By referring to the metallic character of the nanoparticles, the present application is referring to the fact that the electronic structure of the nanoparticles is similar to that of a solid system of the same material. However, the magnetic properties refer to the magnitudes which can be determined via analysis with SQUID (Superconducting Quantum Interference Device) which are mainly remanent magnetization ($M_R$) and coercivity ($H_c$) (represented in FIG. 1); both magnitudes provide an idea of the magnetic character of the samples.

By way of explanation, accelerated electric charges produce an electromagnetic field. In particular, the electromagnetic-field generator of the present invention produces fields having a frequency ranging between the very low frequency (VLF) signals and the super-high frequency (SHF) signals, the latter corresponding to the medium microwave band; said signals preferably range between low frequency (LF) and ultra-high frequency (UHF). Table 1 gives details of the radio-frequency ranges of each one of the bands. Apart from controlling the frequency, the radio-frequency generator is capable of producing the electromagnetic field with a controlled intensity.

TABLE 1

Division into bands of the radio-frequency electromagnetic spectrum

| Frequency | Abbreviation | Frequency range | Wavelength |
|---|---|---|---|
| Extra low | ELF | 3-30 Hz | $10^5$-$10^4$ km |
| Super low | SLF | 30-300 Hz | $10^4$-$10^3$ km |
| Ultra low | ULF | 300-3000 Hz | $10^3$-$10^2$ km |
| Very low | VLF | 3-30 kHz | $10^2$-10 km |
| Low | LF | 30-300 kHz | 10-1 km |
| Medium | MF | 300-3000 kHz | 1-0.1 km |

TABLE 1-continued

Division into bands of the radio-frequency electromagnetic spectrum

| Frequency | Abbreviation | Frequency range | Wavelength |
|---|---|---|---|
| High | HF | 3-30 MHz | 100-10 m |
| Very high | VHF | 30-300 MHz | 10-1 m |
| Ultra high | UHF | 300-3000 MHz | 1-0.100 m |
| Super high | SHF | 3-30 GHz | 100-10 mm |
| Extra high | EHF | 30-300 GHz | 10-1 mm |

The frequency to be applied in each particular case depends on the type of nanoparticle that one wishes to heat, as an example and without this limiting the scope of the present invention:

In the case of magnetic-based nanoparticles which can be functionalized with various ligands, the magnetic fields necessary for producing heating of same should have a frequency of between 100 kHz and 1 GHz, with a magnetic field intensity of between 0 and 15 kA/m.

The noble-metal nanoparticles, such as for example gold or palladium, can be functionalized with various ligands, amongst them compounds of biological interest, which may be responsible for the appearance of a ferromagnetic behaviour as well as the typical metallic behaviour. In this case, in order to heat them, it is necessary to subject them to electromagnetic fields higher than 1 GHz. In this case, the antenna/amplifier combination should apply powers of up to 10 W.

The element for transmitting radio-frequency signals which forms part of the device of the invention can adopt various forms and sizes depending on the frequency of the electromagnetic field which is applied in each case and depending on the geometry of the wave front which is transmitted. Without this limiting the scope of the present invention, it may comprise an emitting antenna, a spiral, a solenoid or a resonant cavity. This transmitter is characterized by its having a transmitting antenna capable of focusing and concentrating the generated electromagnetic field in a region of space. So as to make good use of the energy output of the nanoparticles and the power of the generated electromagnetic field, it is of great importance to manage to focus and concentrate said field. At the same time, this possibility would be of great benefit when working with signals which have a certain potential for damaging healthy tissues as the less these tissues are exposed to radiation the better.

The device of the invention also incorporates a direct temperature measurement system which, without this limiting the scope of the present invention, may consist of a detector for detecting the infrared radiation emitted by the nanoparticles, or it may consist of a thermocouple based on the Seebeck effect.

The Seebeck effect is a thermoelectric effect stemming from the fact that a temperature difference between two metals connected to one another generates a difference in power at the junction of the two metals; from said power difference and knowing one of the two temperatures, which is taken as a reference, it is therefore possible to know the temperature of the other metal.

Optionally, the device of the invention may be placed in a Faraday cage, which consists of an enclosed volume designed to exclude external electromagnetic fields and/or to prevent electromagnetic fields generated inside it from escaping to the outside, keeping the electromagnetic radiation confined in a volume without it affecting measuring equipment and/or personnel.

The Faraday cage is a direct application of Gauss's law. A conductive material delimits a volume so that any electromagnetic field which attempts to enter or leave it cannot do so due to the fact that the electric charge will be distributed at the surface of the conductor.

The device of the invention can act on a group of one or more nanoparticles, raising their temperature as a function of the frequency and intensity of the field, whether due to hysteresis, Foucault currents, or friction and relaxation; consequently it may be used for the controlled heating of a particular area of space, and this has important applications in fields such as the modification of nanometric systems.

In this field, as an example and without this limiting the scope of the present invention, there is a potential application when it comes to modifying the structure on a nanometric scale of systems developed in molecular electronics by utilizing the increase in atomic vibrational energy of the system on application of a radio-frequency field, as well as modifying the magnetic properties of said devices.

This device may be used to investigate the mechanisms and source of the heating of the nanoparticles in the application of hyperthermia treatments in biomedicine, such as, for example, in the destruction of protein aggregates in amyloidosis or in the treatment of tumours using nanoparticles capable of binding to very specific targets or in the controlled release of drugs, amongst other applications.

The radio-frequency transmitting antennas or devices do not emit isotropically, that is to say uniformly in all directions in space. In these antennas, there are areas where the radiation is concentrated in regions, normally in the form of lobes.

The device of the invention, through the geometric design of different antennas, may be used to carry out studies into new field transmission systems for directing said field and concentrating it in particular regions of space so as to avoid irradiating unwanted areas, which is very helpful when it comes to improving hyperthermia applications.

The direct temperature measurement system incorporated in the device of the invention, preferably using infrareds or being based on the Seebeck effect, allows greater control of the temperature, thus overcoming one of the major problems of application of the hyperthermia systems currently existing in biomedicine.

A. Prototype of Hyperthermia Device

An embodiment of the invention consists of the following set of instruments: a radio-frequency field generator Agilent 8648D which works in the range from 9 kHz to 4 GHz with a resolution of 0.001 Hz, the output signal of which is in the power range from +10 to −136 dBm for all frequencies. The output port of the radio-frequency generator is connected to the input port of a solid-state radio-frequency amplifier (Amplifier Research 5S1G4) by means of a coaxial cable. Both the input and output ports of the generator and amplifier respectively, and the ends of the coaxial cable have N-type connectors; especially designed to produce minimum insertion losses (a maximum of 0.2 dB) in microwave signals of up to 10 GHz; the impedance of the connectors is 50 O.

The radio-frequency amplifier used in this example can amplify signals, the frequency of which is from 0.8 GHz to 4.2 GHz. For an input signal coming from the generator whose power is 1 mW, the amplifier will produce an output signal of 6.5 W: equivalent to a gain of 37 dB. A condition which has to be met by any amplifier used is the faithful reproduction of any frequency, amplitude or pulse modulation of the input signal coming from the radio-frequency generator. The output port of the amplifier is also type N.

By means of a coaxial cable having N-type connectors at the ends, the output port of the amplifier is connected to the transmitting device, which in this case consists of a copper spiral 29 mm in diameter and 2 mm in section. The spiral has a resonance frequency of 2.61 GHz, being in the working range of the generator and amplifier. In the case of a spiral, the magnetic component of the electromagnetic field in the centre of same is determined by the Biot-Savart Law: the magnetic induction will be perpendicular to the plane of the spiral and its intensity and direction will depend on the intensity and direction of current passing through the spiral. The spiral is placed on a disc-shaped Teflon support 40 mm in diameter and 12 mm thick (its magnetic permeability is very similar to that of air), on which a circular indentation (2 mm deep and having a diameter which coincides with that of the spiral) has been made so that the plane of the spiral coincides with the plane of the Teflon surface. In the centre of the disc, there is a circular recess 15 mm in diameter and 1 mm deep where liquid samples may be placed; its diameter coincides with the diameter of the circle which defines the focus area of the infrared pyrometer which will be used as temperature sensor.

The pyrometer (Fluke 572 CF) has optics designed to pick up the infrared radiation in a small region of an object at a distance of up to 30 cm; this device is capable of measuring temperatures between −30 and 900° C. It also has a laser beam which defines the area on which measurement of the temperature is being taken.

The combination of copper spiral and Teflon disc is placed inside a Faraday cage; the side measurements of the cage are an order of magnitude greater than the characteristic wavelength of the electromagnetic field emitted by the spiral. For the frequencies which are used in the example, the electromagnetic field has a wavelength of approximately 0.1 m; this means that the Faraday cage should have side dimensions in the order of 1 m. An opening is made in the top side of the cage to facilitate the direct measurement of the temperature using the pyrometer. So as to prevent the electromagnetic field from propagating through the opening, this should have a diameter of less than 2 cm.

The thermocouple is used to calibrate the pyrometer. Before applying the electromagnetic field, the temperature of the sample is measured directly using the thermocouple. The reading of the pyrometer is adjusted to this value by modifying the value of the emissivity: each sample has a different emissivity in the infrared region. In this case, the emissivity is the intensity of infrared radiation emitted by a body at a given temperature.

B. Nanoparticles

The nanoparticles used in this example are:
(a) Gold nanoparticles functionalized with triphenylphosphine and halide ligands. Clusters of 55 atoms of gold (Au) having a diameter of 1.4 nm and clusters of 11 atoms having a diameter of 0.8 nm were studied. These nanoparticles were used dissolved in a commercial buffer HEPES-NaOH with a pH=7.5.
(b) Gold nanoparticles synthesized using a variant of Brust's synthesis (A. C. Templeton, S. Chen, S. M. Gross, R. W. Murray, Langmuir 15 (1999) 66) so that they are functionalized with a biomolecule containing a thiol group: thiopronine. These nanoparticles are soluble in water and are therefore of potential biological interest and serve as a model for nanoparticles functionalized with biomolecules of therapeutic interest.

C. Heating of The Nanoparticles:

With the device specified above, the changes in temperature of the two types of gold nanoparticle as described (a and b) are measured, applying a frequency of the electromagnetic field of 2.61 GHz, frequency which corresponds with the main resonance frequency of the spiral; at this frequency, there is maximum transfer of energy to the spiral so that losses of the signal are minimized.

The results are detailed in Table 2. This table shows the potentiality of the nanoparticles for hyperthermia treatments and the functionality of the designed device.

TABLE 2

Results of studies of hyperthermia in gold (Au) nanoparticles functionalized with various ligands

| Sample | $T_{initial}$ (° C.) | $T_{final}$ (° C.) |
| --- | --- | --- |
| Water | 20.0 | 21.6 |
| HEPES buffer | 20.4 | 25.5 |
| Au55-phosphine | 21.0 | 31.3 |
| Au55-diluted phosphine | 21.4 | 28.9 |
| Au11-phosphine | 18.0 | 31.0 |
| Au-thiopronine ($F_{NP}$~3.0 nm) | 18.0 | 21.0 |
| Au-thiopronine ($F_{NP}$~4.5 nm) | 17.8 | 20.8 |

As can be seen in Table 2, in all cases there is heating of the nanoparticles of between 3.0° C., obtained for the nanoparticles of Au-thiopronine ($F_{NP}$~3.0 nm and 4.5 nm), and 13.0° C. obtained for the nanoparticles of Au11-phosphine, which demonstrates to us the potentiality of all of them to be heated under the action of radio-frequency electromagnetic fields and the functionality of the device of the invention.

All publications, patent and patent applications cited herein or filed with this application, including references filed as part of an Information Disclosure Statement are incorporated by reference in their entirety.

The invention claimed is:

1. A hyperthermia system comprising:
a hyperthermia apparatus comprising the following elements:
(a) a generator of a radio-frequency electromagnetic field;
(b) an amplifier of a radio-frequency electromagnetic field;
(c) a transmitter of a radio-frequency electromagnetic field; and
(d) a direct temperature measurement system,
wherein the generator of the radio-frequency electromagnetic field is a network analyzer device which, in addition to generating the signal, allows impedances, coefficients of reflection and transmission and insertion losses to be determined;
the transmitter of the electromagnetic field is capable of focusing and concentrating the electromagnetic field in a defined region; and
a plurality of nanoparticles, wherein said nanoparticles are capable of being heated by the action of a radio-frequency electromagnetic field generated by the hyperthermia apparatus.

2. The system according to claim 1, wherein the nanoparticles are at least one of metallic and magnetic nanoparticles.

3. The system according to claim 1, wherein the nanoparticles are functionalized via metal-sulphur bonds with organic molecules or biomolecules.

4. The system according to claim 2, wherein the nanoparticles are magnetic nanoparticles functionalized directly or functionalized via a coating of noble metal.

5. A method for producing heating and other hyperthermia effects on one or more nanoparticles capable of being heated under the action of a radio-frequency electromagnetic field said method comprising exposing said nanoparticles to heating by a hyperthermia apparatus comprising the following elements:
(a) a generator of a radio-frequency electromagnetic field;
(b) an amplifier of a radio-frequency electromagnetic field;
(c) a transmitter of a radio-frequency electromagnetic field; and
(d) a direct temperature measurement system,
wherein the generator of the radio-frequency electromagnetic field is a network analyzer device which, in addition to generating the signal, allows impedances, coefficients of reflection and transmission and insertion losses to be determined and the transmitter of the electromagnetic field is capable of focusing and concentrating the electromagnetic field in a defined region.

6. A method of heating one or more nanoparticles at a location, wherein the method employs an apparatus which comprises (a) a generator of a radio-frequency electromagnetic field, comprising a network analyzer device which, in addition to generating the signal, allows impedances, coefficients of reflection and transmission and insertion losses to be determined; (b) an amplifier of a radio-frequency electromagnetic field; (c) a transmitter of a radio-frequency electromagnetic field, the transmitter being capable of focusing and concentrating the electromagnetic field in a defined region; and (d) a direct temperature measurement system, the method comprising the steps of:
(i) introducing the nanoparticle at the location; and
(ii) generating a radio-frequency electromagnetic field using the apparatus which has a frequency and/or intensity capable of heating the nanoparticles.

7. The method of claim 6, further comprising the step of determining the temperature at the location of the nanoparticles and optionally adjusting the frequency and/or intensity of the radio-frequency electromagnetic field to modulate the hyperthermic heating effect generated by the apparatus.

8. The method of claim 6, wherein the location is a tissue of a living subject.

9. The method of claim 8, wherein the tissue is tumour tissue and the heating is effective to kill cells of said tumour tissue.

10. The method according to claim 6, wherein the location is an area of protein aggregates in a subject having amyloidosis and the heating is effective to destroy said protein aggregates.

11. The method according to claim 6, wherein the location is an area of drug delivery in a subject administered said drug and the heating is effective to control the release of the drug in said subject.

12. The hyperthermia system according to claim 2, wherein said nanoparticles are functionalized noble-metal nanoparticles.

13. The hyperthermia system according to claim 12, wherein said noble-metal nanoparticles are functionalized via metal-ligand bonds.

14. The hyperthermia system according to claim 12, wherein said noble-metal nanoparticles are protected by surfactant molecules with stabilization via dipolar interactions.

15. The hyperthermia system according to claim 1, wherein the system further comprises a Faraday cage which encloses the elements (a) to (d) of the hyperthermia apparatus for radiation shielding.

16. The hyperthermia system according to claim 1, wherein the system for directly measuring the temperature uses infrared radiation.

17. The hyperthermia system according to claim 16, wherein the system for directly measuring the temperature uses a system based on the Seebeck effect.

18. The hyperthermia system according to claim 1, wherein the system for directly measuring the temperature uses an infrared pyrometer.

19. The heating method according to claim 6, wherein the hyperthermia apparatus further comprises a Faraday cage which encloses the elements (a) to (d) of the hyperthermia apparatus for radiation shielding.

20. The hyperthermia system according to claim 6, wherein the system for directly measuring the temperature uses infrared radiation.

21. The hyperthermia system according to claim 6, wherein the system for directly measuring the temperature uses a system based on the Seebeck effect.

22. The heating method according to claim 6, wherein the system for directly measuring the temperature uses an infrared pyrometer.

* * * * *

UNITED STATES PATENT AND TRADEMARK OFFICE
CERTIFICATE OF CORRECTION

PATENT NO.        : 8,463,397 B2  
APPLICATION NO.   : 12/670493  
DATED             : June 11, 2013  
INVENTOR(S)       : Munoz Marquez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 572 days.

Signed and Sealed this

Eighth Day of September, 2015

Michelle K. Lee  
*Director of the United States Patent and Trademark Office*